United States Patent

Hans

Patent Number: 5,320,096
Date of Patent: Jun. 14, 1994

[54] FILTERING DEVICE AND THE USE THEREOF

[75] Inventor: Lambert Hans, Stockholm, Sweden

[73] Assignee: Gibeck Respiration AB, Uplands Väsby, Sweden

[21] Appl. No.: 993,059

[22] Filed: Dec. 18, 1992

[30] Foreign Application Priority Data

Feb. 21, 1992 [SE] Sweden .................. 9200533

[51] Int. Cl.⁵ .................. A61M 16/10; B01D 27/07; B01D 29/07
[52] U.S. Cl. .................. 128/205.29; 128/201.13; 128/204.15; 55/498; 55/DIG. 35; 210/493.1
[58] Field of Search .................. 128/205.27, 204.15, 128/205.29, 201.13, 207.14, 205.12, 205.17, 200.24; 55/498, DIG. 35, 514; 210/493.1–493.5; 165/119

[56] References Cited

U.S. PATENT DOCUMENTS

| | | | |
|---|---|---|---|
| 3,881,482 | 5/1975 | Lindholm | 128/201.13 |
| 4,798,676 | 1/1989 | Matkovich | 210/767 |
| 4,964,405 | 10/1990 | Arnoth | 128/205.17 |
| 5,022,394 | 6/1991 | Chmielinski | 128/207.14 |
| 5,035,236 | 7/1991 | Kanegaonkar | 128/201.13 |
| 5,042,468 | 8/1991 | Lambert | 128/200.26 |
| 5,158,077 | 10/1992 | Sundström | 128/205.27 |

FOREIGN PATENT DOCUMENTS

| | | | |
|---|---|---|---|
| 149590 | 7/1985 | European Pat. Off. | 128/205.29 |
| 269589 | 6/1988 | European Pat. Off. | 128/205.29 |
| 978870 | 12/1982 | U.S.S.R. | 128/205.27 |

*Primary Examiner*—Edgar S. Burr
*Assistant Examiner*—Eric P. Raciti
*Attorney, Agent, or Firm*—Dressler, Goldsmith, Shore & Milnamow, Ltd.

[57] ABSTRACT

A filtering device for connection to the respiratory tract of a person and comprising a cover (1) enclosing a heat and moisture exchanging material and a bacteria absorbing filter which consists of a folded, air-permeable sheet material. The heat and moisture exchanging material is formed as strips (9) inserted in the pleats of the sheet material (8).

8 Claims, 3 Drawing Sheets

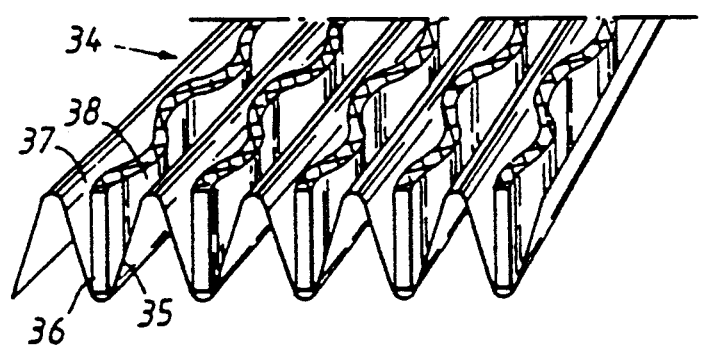

FILTERING DEVICE AND THE USE THEREOF

TECHNICAL FIELD

The present invention relates to a filtering device for connection to the respiratory tract of a person and comprising a cover enclosing a heat and moisture exchanging material and a bacteria-absorbing filter which consists of a folded, air-permeable sheet material. The invention also relates to the use of such a filtering device.

The filtering device according to the invention may be used in connection with respirator care, intensive care and anaesthesia of patients.

PRIOR ART

Patients receiving respirator care are often susceptible to infection. For this reason, it is important to filter the air coming from the respirator from foreign bacteria, virus, etc.

The air coming from the patient is often infected and/or moist. Said air enters the respirator during exhalation, and bacteria and other particles are deposited inside it together with warm and moist condensate. This results in rapid growth of microorganisms and it is therefore necessary to clean and sterilize the respirator at regular intervals and, as a rule, between patients.

For this reason it is important to protect the respirator from the air coming from the patient. U.S. Pat. No. A 3 713 440 and U.S. Pat. No. A 4 063 913 disclose and show examples of filters solving this problem.

As a rule, a so called active humidifier moistens the air of a patient connected to a respirator. This is because the air coming from the respirator is dry and has a relatively low temperature which would make the lungs dry up, if the air was not humidified before it is introduced into the patient.

An active humidifier is usually rather expensive and requires supervision, refilling of water, and maintenance in order to work in a satisfactory way. The air coming from the humidifier will be condensed into the tubing system, which therefore has to be emptied regularly, and the condensate constitutes a breeding ground for microorganisms. For this reason, heat and moisture exchangers (HME) positioned between the patient and the respirator are often used.

Said heat and moisture exchangers operate in such a way that the moisture of the air exhaled by the patient is accumulated and stored in an air-permeable material and thereafter partly evaporates during inhalation and is returned to the patient in the air inhaled.

Examples of such heat and moisture exchangers are disclosed and shown in SE-C 167 364, U.S. Pat. No. A 4 090 513, U.S. Pat. No. A 4 200 094 and GB 2 116 434A.

Said devices have many advantages. They are nonexpensive to manufacture and use, provide excellent humidification as well as dry tubes. However, their bacteria filtering qualities are usually relatively limited and they are therefore not used in cases where this is an essential quality. For this reason, efforts have been made to use bacterial filters instead, which have been placed in the same position as conventional heat and moisture exchangers. Examples of such bacterial filters are shown and disclosed in U.S. Pat. No. A 4 360 018 and GB 2 233 904A.

However, since said bacterial filters consist of a hydrophobic material they have a very limited heat and moisture exchange capacity, inspite of their relatively large filter surface.

Various efforts have been made to compensate for the limited heat and moisture exchange capacity of a good bacterial filter. Examples hereof are shown and disclosed in EP 87 309 070.8 (Publ. No. 0 265 163), PCT application WO 90/141 22 and Swedish patent application 9 000 135-5.

One disadvantage of the known devices is that the volume of the filter container must be increased in order to achieve an adequate heat and moisture exchange capacity For this reason, such a combination of heat/moisture exchanger and bacterial filter will be larger than in the case of a device comprising only a filter with the same filtering capacity. A larger volume restricts the use of the device since it increases the so called dead volume in the respiratory system of the patient. A larger dead volume in the respiratory system gives a greater degree of rebreathing of the patient's exhalation air, resulting in a larger content of carbon dioxide in the air inhaled.

SUMMARY OF THE INVENTION

It is an object of the present invention to provide a filtering device which, at least partly, eliminates the disadvantages of the prior art filtering devices and which takes up a small volume while still having good bacteria-filtering and heat/moisture exchanging qualities.

This object is achieved by the filtering device according to the invention having the features stated in the characterizing portion of claim 1.

DESCRIPTION OF THE FIGURES

FIGS. 4–6 are perspective views of three different arrangements of a part of a filtering device according to the invention.

PREFERRED EMBODIMENTS

Figure 1:
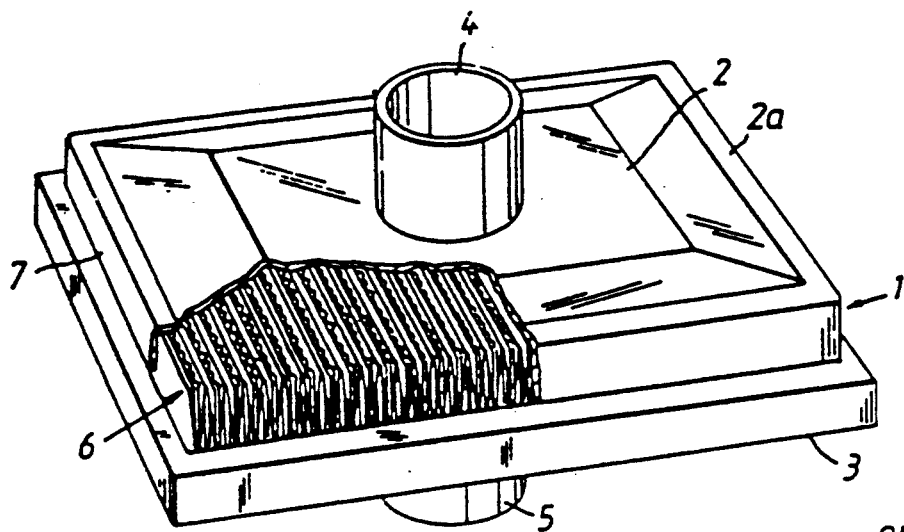
FIG. 1 is a perspective view, partly in section.

FIG. 1 shows the filtering device consisting of a substantially parallel-epipedic cover 1 with two opposing end walls 2 and 3, which are provided with inlet and outlet connection pieces 4 and 5, as well as of a filter package enclosed in the cover 1.

The filtering device is intended to be connected, via the connection piece 4, to a tracheal tube (not shown), either direct or, for example, via a tube, and via the connection piece 5 to a mechanical breathing device, such as a respirator (not shown) or anaesthesia apparatus for example, via a Y-piece. In certain applications, the connection piece may be permitted to open straight into the atmosphere.

The end walls 2 and 3 of the cover 1 are provided with frames of which only the frame 2a of the end wall 2 is shown in the figure. Said frames are situated closer to one another than the central surfaces of the end walls, clamping between them the filter package 6 in the cover 1, which is divided at 7 to facilitate insertion of the filter package into the cover.

The filter package 6 which is of essentially parallel-epipedic shape entirely fills the space in the cover with the exception of a small space between the end wall 2 of the cover inside the frame 2a and the upper side of the filter package and a corresponding space at the lower side of the filter package The filter package 6 seals against the frame 2a and against the corresponding frame on the end wall 3.

The filter package 6 comprises two components, i.e. a folded sheet material 8 and a strip material 9. The sheet material 8 is folded into a staggered shape with parallel and relatively sharp folds. However, other shapes, such as the below described shapes according to other embodiments, are also possible. The composition of the sheet material may be selected amongst a plurality of materials which are permeable to air but impermeable to bacteria. Examples of such materials will be described later. The strip material 9 consists of strips of micro-corrugated paper, i.e. folded paper 9a, optionally glued to a plane sheet of paper 9b, but other shapes are possible, for example, the below described shapes according to other embodiments. The composition of the strip material may be selected amongst a plurality of materials which are air-permeable and hydrophilic and which therefore have a good heat and moisture exchange capacity.

Figure 1A:
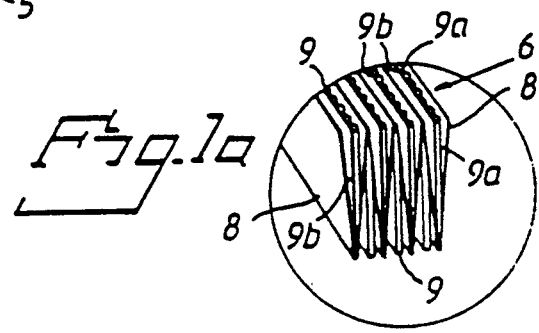
FIG. 1a is a partial perspective view of a first embodiment of a filtering device according to the present invention.

The strips 9a, b are rectangular and have essentially the same extension as the space between two pleats of the sheet material. They take up a considerably part of the space between the pleats of the sheet material 8, either on both sides of the same, as shown in FIGS. 1 and 1a, or only on one side of the same and, if so, suitably on the side closest to the patient. Optionally, the strips 9a, b may be folded, extending over a plurality of pleats of the sheet material 8. If the sheet material 9 with interposed strips 9a, b is compressed with great force transversely to the plane of the strips and is thereafter inserted in the cover 1, it is not necessary to attach the strips to the sheet material by means of, for example, gluing.

Figure 2:
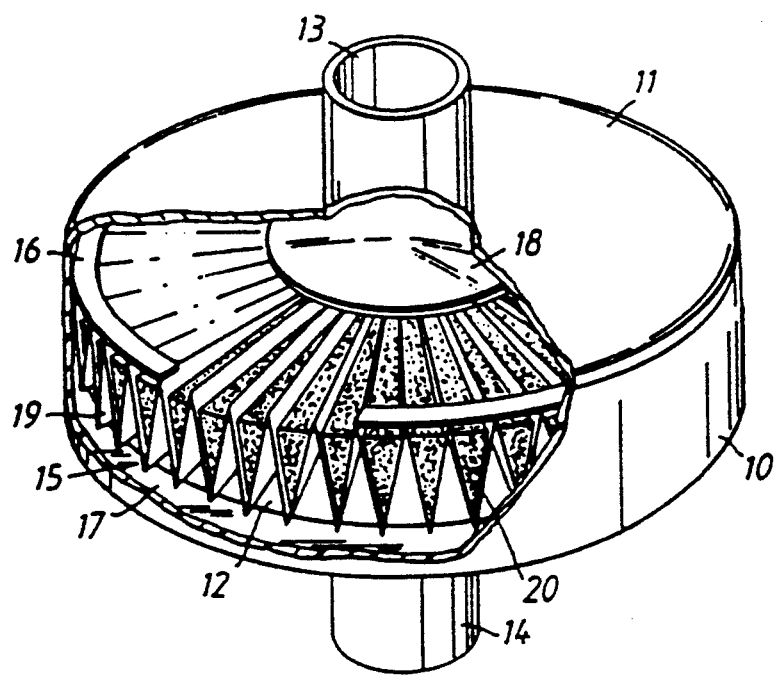
FIGS. 2 and 3 are perspective views, partly in section, of two other embodiments of a filtering device according to the invention.

FIG. 2 shows the filtering device consisting of a substantially circular-cylindrical cover 10 composed of two cover halves and having two opposing end walls 11 and 12, which are provided with inlet and outlet connection pieces 13 and 14, and of a filter package 15 enclosed in the cover 10.

The filtering device of FIG. 2 is intended to be connected via the connection pieces 13, 14 in the same way as the device shown in FIG. 1. The end walls 11, 12 of the filtering device of FIG. 2 are situated near the filter package 15 to reduce the dead space in the device. The filter package 15 is held in position within the cover 10 between outer annular flanges 16 and 17 thereon and between two interconnected circular plates (of which only plate 18 is shown). Said plates may be of curved or conical shape in order to spread incoming air evenly over the filter package 15 with a minimum of resistance to flow.

The filter package 15 has two components, namely a folded sheet material 19 and a strip material 20. The sheet material 19 is folded into a staggered shape with sharp folds. Further, the sheet material is fan-shaped with radially extending pleats. The composition of the sheet material 19 will be described later. The strip material 20 consists of foamed plastic or other hydrophilic, air-permeable material and has a rectangular cross section, which during mounting in all the pleats of the sheet material is compressed into a parallel-trapezoidal triangular section or which was given, at the time of manufacture, a parallel-trapezoidal or triangular cross section. FIG. 2 shows strips 20 situated only in every other pleat of the strip material 19 which strips, however, may be inserted in all of the pleats, if required The length of the strips substantially corresponds to the length of the pleats and the strips are clamped in or glued onto the sheet material. The strips 19 also act as distance elements for keeping the pleats of the sheet material spaced apart at a substantially constant distance.

Figure 3:
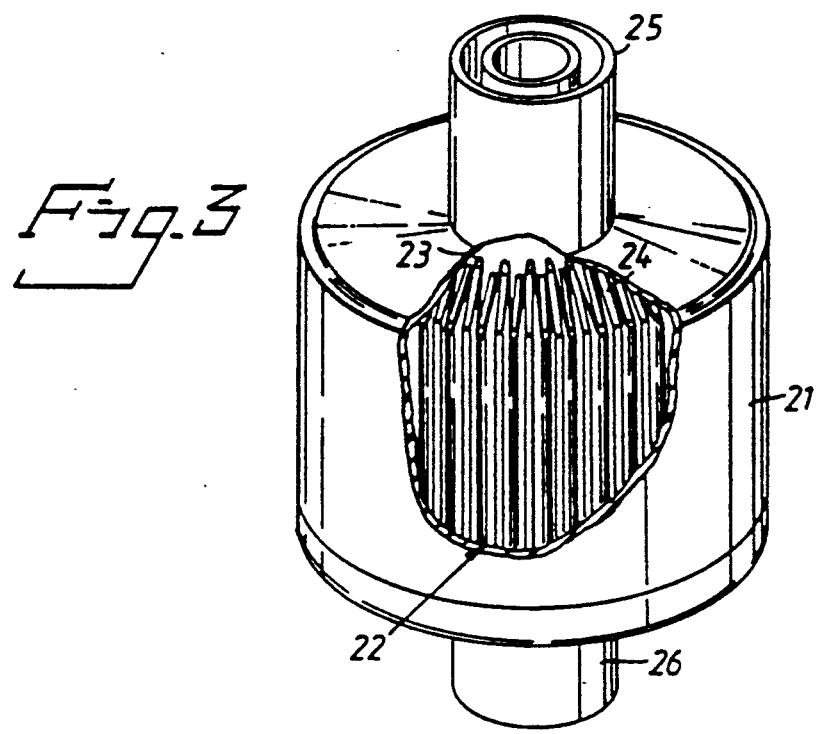

FIG. 3 shows the filtering device substantially corresponding to the one of FIG. 2 with a cover 21 and a therein enclosed filter package 22 consisting of a folded sheet material 23 and strips 24 inserted in all the pleats of the sheet material and held therein The strips 24 on either one of the two sides of the sheet material may comprise one or more interconnected folded strips inserted in and having the same extension as the pleats of the sheet material. The filtering device 21-23 is fan-shaped as is the filtering device of FIG. 2 but with axially disposed pleats. Means (not shown) in the cover 21 ensure that all air flow passes the sheet and strip materials 23, 24 in an essentially uniform manner after entering an inlet connection piece 25 and before escaping through an outlet connection piece 26.

Figure 4:
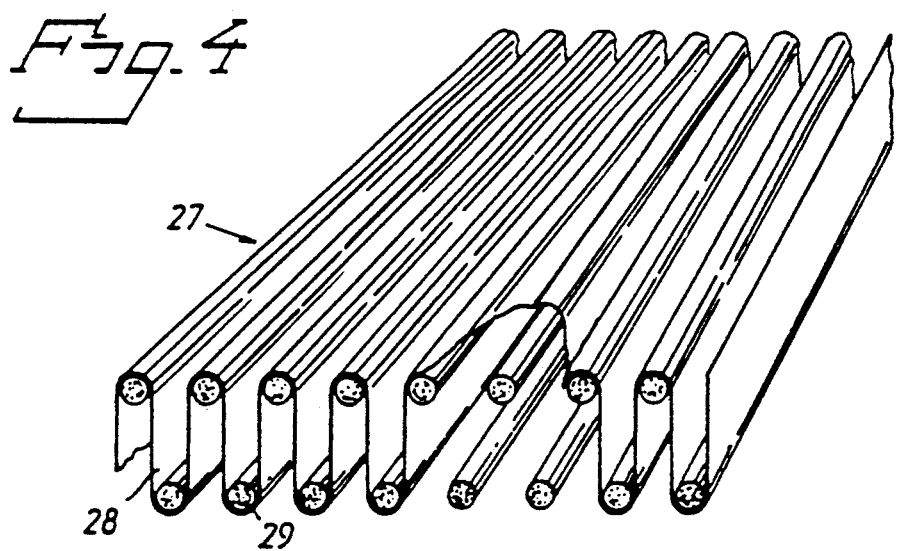

FIG. 4 shows a filter package 27 which may be inserted into a cover (not shown), such as any one of the above described, and may be given a concertina or fan shape. The filter package 27 consists of a waved, folded sheet material 28 with parallel pleat walls and strips inserted in the pleats in the form of hydrophilic, air-permeable bars 29 of circular section of a size corresponding to the shape of the pleat base.

Figure 5:
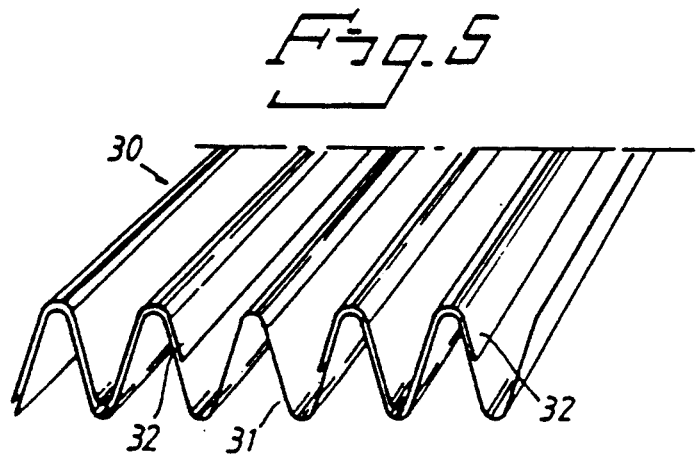

FIG. 5 shows a filter package 30 which may be inserted in a cover (not shown) such as any one of the above described, and which may be formed, for example, into a fan shape. The filter package 30 consists of a sheet material 31 folded into a staggered shape and a strip material 32 inserted in the pleats thereof. The material 32 is folded into essentially the same shape as the sheet material 31, and extends over several pleats of the same and, in some applications, may extend over the whole of the sheet material, the sheet material and the strip material being of essentially identical shape.

FIG. 6 shows a filter package 34 which may be inserted into a cover (not shown), such as any one of the above described. The filter package 34 consists of a sheet material 35 folded into a staggered shape and a strip material 36 inserted into the pleats thereof. The material 36 is folded or waved, the tops and the troughs of the waves being parallel to the respiratory air entering transversely to the sheet material 35 (i.e. from above in FIG. 6). The material 36 has relatively low air permeability or none at all and is preferably water absorbing and retaining. It may consist of cardboard or foamed plastic. Owing to the material 36 having little or no air permeability, a gap is required between said material and the sheet material 35 in order for the air to pass more or less freely through the air-permeable sheet material. Two such gaps 37 and 38 are shown in FIG. 6 on both sides of the strip 36.

Common to all the embodiments described above and shown on the drawings is that the sheet material is folded and that the strip material is inserted into the pleats in order to provide a large surface along which an essential part of the air passing through the filter package must flow to be humidified and heated or dehumidified and cooled. Further, they have in common that the folded sheet material acts as a carrier for the strip material.

The sheet materials included in the above described filter packages may be selected amongst a large number of available materials, which are tight to bacteria but permeable to air. The material may be hydrophobic or hydrophilic and may consist of a matrix of hydrophobized glass fibres compressed into a higher density Other suitable materials may be cellulose paper, polysulphone, electrostatically charged polypropylene fibres or thin polycarbonate fibres.

The strip materials included in the filter packages may be selected amongst a large number of available materials, which are hydrophilic and usually air-permeable. The material may consist of foamed polyurethane with open pores or with pores which are shaped in various ways to let the respiratory gas pass along the material Further, the material may consist of relatively loosely packed polyethylene or polyester fibres or may be cardboard or paper of glass fibres or cellulose with waved or plane surface The efficiency of the strip material may be considerably increased if treated with a hydrophilic substance such as LiCl, $CaCl_2$, polyacrylic acid, polyvinyl pyrrolidone, polyvinyl alcohol or other hydrophilic polymers, glycol or glycerine.

While only a few embodiments of the present invention have been described above and shown on the drawings, it will be understood that several other embodiments are also possible without departing from the scope of the invention. Therefore, the invention is only limited by what is stated in the claims.

I claim:

1. A filtering device for connection to the respiratory tract of a person and comprising a cover enclosing separate strips of a heat and moisture exchanging material and a bacteria absorbing filter which consists of a folded, air-permeable pleated sheet material, the strips of heat and moisture exchanging material being disposed in a plurality of the pleats of the sheet material, which pleats act as a carrier for the separate strips that take up a substantial part of the space between the pleats of the sheet material in which they are located and which extend along substantially the whole length of a pleat to space adjacent pleats from each other.

2. A filtering device according to claim 1, wherein the strips are disposed on both sides of the sheet material.

3. A filtering device according to claim 1, wherein the sheet material is folded into a staggered shape and is given one of a fan-like, circular shape and a generally rectangular shape.

4. A filtering device according to claim 1, wherein the cross-sectional shape of the strips is essentially the same as that of the pleats.

5. A filtering device according to claim 1, wherein the strips are folded or waved and consist of a material with little or no air permeability and that large parts of the folded surfaces of the strips are spaced apart from the sheet material.

6. A filtering device according to claim 1, wherein the sheet material consists of one of the following materials: cellulose paper, hydrophobized glass fibres, polysulphone, electrically charged polypropylene fibres and thin polycarbonate fibres.

7. A filtering device according to claim 1, wherein the strips consist of an air-permeable material, such as foamed polyurethane, loosely packed polyethylene or polyester fibres, or folded paper, which material is preferably treated with a hydrophilic substance.

8. A filtering device according to claim 7, wherein the air permeable material is treated with a hydrophilic substance.

* * * * *